US012791448B2

(12) United States Patent
Mizutani et al.

(10) Patent No.: US 12,791,448 B2
(45) Date of Patent: Nov. 10, 2026

(54) GAS MEASURING INSTRUMENT

(71) Applicant: SINTOKOGIO, LTD., Nagoya (JP)

(72) Inventors: Manase Mizutani, Nagoya (JP); Yoshihisa Suzuki, Nagoya (JP)

(73) Assignee: SINTOKOGIO, LTD., Nagoya (JP)

( * ) Notice: Subject to any disclaimer, the term of this patent is extended or adjusted under 35 U.S.C. 154(b) by 271 days.

(21) Appl. No.: 18/699,010

(22) PCT Filed: Sep. 13, 2022

(86) PCT No.: PCT/JP2022/034284
§ 371 (c)(1),
(2) Date: Apr. 5, 2024

(87) PCT Pub. No.: WO2023/067955
PCT Pub. Date: Apr. 27, 2023

(65) Prior Publication Data

US 2024/0410795 A1 Dec. 12, 2024

(30) Foreign Application Priority Data

Oct. 18, 2021 (JP) ................................ 2021-170308

(51) Int. Cl.
*G01N 1/22* (2006.01)
*B01D 53/04* (2006.01)
*G01N 33/00* (2006.01)

(52) U.S. Cl.
CPC ........... *G01N 1/2205* (2013.01); *B01D 53/04* (2013.01); *G01N 33/0027* (2013.01); *B01D 2253/112* (2013.01)

(58) Field of Classification Search
CPC .. G01N 1/2205; G01N 33/0027; G01N 27/12; G01N 33/0014; B01D 53/04; B01D 2253/112
See application file for complete search history.

(56) References Cited

U.S. PATENT DOCUMENTS 5,891,220 A * 4/1999 Gary ..................... B01D 53/04 95/138
6,506,351 B1 * 1/2003 Jain ....................... B01D 53/06 423/239.1

(Continued)

FOREIGN PATENT DOCUMENTS

EP 1005904 A2 * 6/2000 ............. B01D 53/02
EP 1 148 337 A2 10/2001

(Continued)

OTHER PUBLICATIONS

Extended European Search Report issued Sep. 12, 2025 in Application No. 22883265.5.

(Continued)

*Primary Examiner* — Francis C Gray
(74) *Attorney, Agent, or Firm* — Faegre Drinker Biddle & Reath LLP

(57) ABSTRACT

The gas measuring device includes a filter configured to remove background gas from sample gas in an atmosphere, and a gas sensor configured to detect target gas from the sample gas passed through the filter, wherein the background gas is at least one kind of gas selected from nitrogen gas, oxygen gas, and rare gases.

4 Claims, 2 Drawing Sheets

(56) References Cited

U.S. PATENT DOCUMENTS

| | | | | |
|---|---|---|---|---|
| 7,604,683 | B2 * | 10/2009 | Mukaide ................ | B01D 53/02<br>95/103 |
| 2001/0044154 | A1 | 11/2001 | Evans | |
| 2006/0278077 | A1 * | 12/2006 | Mukaide ............. | C01B 23/0052<br>95/96 |
| 2022/0296845 | A1 * | 9/2022 | Jackson ............ | A61M 16/0833 |

FOREIGN PATENT DOCUMENTS

| | | | |
|---|---|---|---|
| JP | H01-57739 | B2 | 12/1989 |
| JP | H02-075951 | A | 3/1990 |
| JP | H6-265507 | A | 9/1994 |
| JP | 2001-000822 | A | 1/2001 |
| JP | 2006-313105 | A | 11/2006 |
| JP | 2014-166971 | A | 9/2014 |
| JP | 2017-083337 | A | 5/2017 |
| JP | 2017-122661 | A | 7/2017 |
| JP | 2017-149683 | A | 8/2017 |
| JP | 2019-147697 | A | 9/2019 |
| JP | 2020-041833 | A | 3/2020 |

OTHER PUBLICATIONS

Voldum-Clausen K., “Effective removal of oxygen from nitrogen carrier gas in gas-liquid chromatographic analysis,” Jun. 1996, p. 500-p. 502, XP093310787.

International Preliminary Report on Patentability mailed May 2, 2024, for PCT/JP2022/034284.

Japanese Office Action dated Dec. 27, 2024 in Application No. 2021-170308.

* cited by examiner

GAS MEASURING INSTRUMENT

TECHNICAL FIELD

The present disclosure relates to a gas measuring device.

BACKGROUND ART

Patent Document 1 discloses a gas measuring device. The gas measuring device includes a dehumidification cell that performs dehumidification of the sample gas and removal of ethanol in the sample gas, a concentration cell that concentrates the target gas in the dehumidified sample gas by adsorption and desorption, and a MEMS gas sensor that detects the concentrated target gas.

CITATION LIST

Patent Document

Patent Document 1: Japanese Patent Application Publication No. patent publication No. 2020-041833

SUMMARY OF INVENTION

Technical Problem

The gas measuring device described in Patent Document 1 cannot remove nitrogen gas, oxygen gas, and rare gases, which are main component gases other than water vapor in the atmosphere. Therefore, the gas measuring device described in Patent Document 1 may not be able to detect a trace amount of target gas contained in the atmosphere. The present disclosure provides a gas measuring device capable of improving detection accuracy of target gas in the atmosphere.

Solution to Problem

A gas measuring device according to an aspect of the present disclosure includes a filter configured to remove background gas from sample gas in an atmosphere, and a gas sensor configured to detect target gas from the sample gas passed through the filter. The background gas is at least one kind of gas selected from nitrogen gas, oxygen gas and rare gases.

According to the gas measuring device, at least one kind of gas selected from nitrogen gas, oxygen gas and rare gases is removed from sample gas in the atmosphere by a filter, and target gas is detected from the sample gas by a gas sensor. As described above, since the main component gases in the atmosphere are removed by the filter, the target gas is relatively concentrated. Therefore, the gas measuring device can improve the detection accuracy of the target gas in the atmosphere.

In one embodiment, the filter may be a porous metal complex in which a metal ion and an organic ligand are bonded. The porous metal complex is less likely to act electrically than a general adsorption member and can remove low-molecular-weight gases. The gas measuring device may appropriately remove nitrogen gas, oxygen gas, and rare gases by using the porous metal complex as a filter.

In one embodiment, the filter may include a breathable bag configured to contain the porous metal complex in powder form. In this case, the gas measuring device can adjust the amount and accommodation form of the porous metal complex according to the flow rate of the passing sample gas or the shape of the flow path, and can reduce the risk that the porous metal complex in powder form diffuses into the measurement system or the atmosphere.

In one embodiment, the filter may have a container configured to accommodate the porous metal complex in powder form, and the container may include an injection port for injecting the sample gas and an exhaust port for exhausting the sample gas. In this case, the gas measuring device can reduce the risk of diffusion of the porous metal complex in powder form into the measurement system or the atmosphere.

In one embodiment, the filter may include a first filter formed of the porous metal complex that mainly removes oxygen gas and a second filter disposed downstream of the first filter and formed of the porous metal complex that mainly removes nitrogen gas and rare gases. With such a configuration, for example, when the filter needs to be replaced for maintenance, the operator does not need to replace the entire filter and can replace only the filter that needs maintenance. Therefore, the gas measuring device can improve the maintainability.

In one embodiment, the first filter may be formed of a porous metal complex in which a metal ion and tetracyanoquinodimethane are bonded, and the second filter may be formed of a porous metal complex in which metal ion and terephthalic acid are bonded or metal ion and methylene are bonded. Since the relatively low molecular weight tetracyanoquinodimethane and the relatively low molecular weight terephthalic acid or methylene are used as the ligand, the gas measuring device may reduce the gap in the porous metal complex. Therefore, the gas measuring device can selectively take in only low-molecular-weight gases from the sample gas.

Advantageous Effects of Invention

According to the gas measuring device of the present disclosure, it is possible to improve target gas in the atmosphere can be improved.

DESCRIPTION OF EMBODIMENTS

Figure 1:
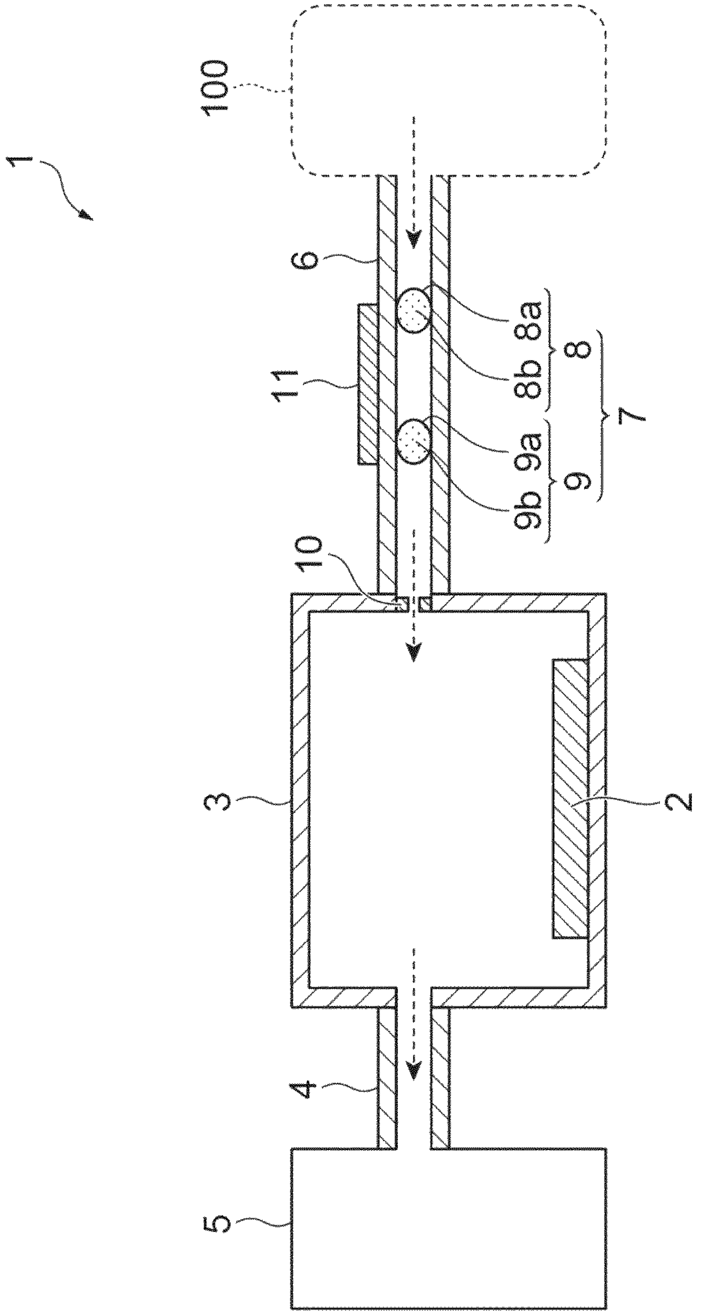
FIG. 1 is a schematic diagram illustrating an example of a gas measuring device according to an embodiment.

Hereinafter, embodiments of the present disclosure will be described with reference to the drawings. In the following description, the same or corresponding elements are denoted by the same reference numerals, and redundant description will not be repeated. The dimensional ratios in the drawings are not necessarily consistent with those in the description. The terms “up”, “down”, “left” and “right” are based on the illustrated state and are for convenience.

[Configuration of Gas Measuring Device]

FIG. 1 is a schematic diagram illustrating an example of a gas measuring device according to an embodiment. A gas measuring device 1 shown in FIG. 1 is a device for detecting target gas from sample gas 100. The sample gas 100 is gas in the atmosphere, and mainly contains at least one gas selected from nitrogen ($N_2$) gas, oxygen ($O_2$) gas, and rare gases. The rare gases is, for example, helium (He) and neon (Ne). The sample gas 100 may include water vapor or $H_2$ gas. The sample gas 100 may be acquired from a closed space.

As shown in FIG. 1, the gas measuring device 1 includes a gas sensor 2. The gas sensor 2 may be any gas sensor of a semiconductor type, an electrochemical type, a quartz oscillator type, or the like. The gas sensor 2 is configured to detect a target gas contained in the sample gas 100. The target gas is, for example, acetic acid ($CH_3COOH$), but is not limited thereto.

The gas sensor 2 is housed inside a chamber 3. The chamber 3 is connected to a vacuum pump 5 via an exhaust pipe 4, and the internal space is decompressed. A suction pipe 6 is connected to the chamber 3. When the vacuum pump 5 decompresses the interior space of the chamber 3, the sample gas 100 is drawn from the suction pipe 6 into the interior space of the chamber 3. The gas sensor 2 detects the target gas from the sample gas 100 drawn into the interior space of the chamber 3.

On the upstream side of the gas sensor 2, here inside the suction pipe 6, a filter 7 is placed. The filter 7 removes background gas from the sample gas 100. The filter 7 may remove the background gas from the sample gas 100 without adsorbing the target gas. The background gas is gas other than the target gas. The background gas is at least one kind of gas selected from $N_2$ gas, $O_2$ gas, and rare gases.

The filter 7 has a first filter 8 and a second filter 9. The first filter 8 has a breathable bag **8*a*. The bag 8*a* is formed of a nonwoven fabric, for example. The shape of the bag 8*a* can be adjusted to fit against the interior wall of the suction pipe 6. The bag 8*a* contains porous metal complex 8*b* in powder form therein. The porous metal complex 8*b* is a compound in which a metal ion and an organic ligand are bonded. The porous metal complex 8*b* is a metal-organic framework (MOF: Metal Organic Framework) or a porous coordination polymer (PCP: Porous Coordination Polymer). The porous metal complex 8*b* may also be zeolite or porous silica. The porous metal complex 8*b* primarily removes oxygen gas and water vapor as an example. The porous metal complex 8*b*** may be, for example, a porous metal complex in which metal ion and tetracyanoquinodimethane (TCNQ) are bonded. As the metal ions, ions of a type in which coordination is unsaturated may be selected.

The second filter 9 is disposed downstream of the first filter 8. The second filter 9 has a breathable bag **9*a*. The bag 9*a* is formed of a nonwoven fabric, for example. The shape of the bag 9*a* can be adjusted to fit against the interior wall of the suction pipe 6. The bag 9*a* contains porous metal complex 9*b* in powder form therein. The porous metal complex 9*b* is a compound in which a metal ion and an organic ligand are bonded. The porous metal complex 9*b* is a metal-organic framework or a porous coordination polymer. The porous metal complex 9*b* primarily removes nitrogen gas and rare gases by way of example. The porous metal complex 9*b* may be, for example, a porous metal complex in which metal ions are bonded to terephthalic acid or methylene. As the metal ions, ions of a type in which coordination is unsaturated may be selected. Note that the suction pipe 6 may be formed of a soft tube. In this case, the first filter 8 and the second filter 9** can be easily placed and taken out.

A partition member 10 may be provided between the chamber 3 and the filter 7. The partition member 10 is, for example, a member which is disposed at a connection port between the chamber 3 and the suction pipe 6 and has an inside diameter smaller than that of the suction pipe 6. By providing the partition member 10, the filter 7 is prevented from being pushed into the chamber 3 by the pressure of the suction pipe 6.

The gas measuring device 1 may include a temperature regulator 11 for adjusting the temperature of the filter 7. The temperature regulator 11 is, for example, a heater provided in the suction pipe 6. Since the suction pipe 6 is heated by the temperature regulator 11, the background gas adsorbed to the porous metal complexes **8*b* and 9*b* can be removed from the porous metal complexes 8*b* and 9*b***.

[Operation of Gas Measuring Device]

When the vacuum pump 5 operates, the internal space of the chamber 3 is decompressed. This draws the sample gas 100 into the suction pipe 6. The drawn sample gas 100 passes through the first filter 8. At this time, oxygen gas and water vapor contained in the sample gas 100 are removed by the porous metal complex **8*b* of the first filter 8. Subsequently, the sample gas 100 passes through the second filter 9. At this time, nitrogen gas and rare gases contained in the sample gas 100 are removed by the porous metal complex 9*b* of the second filter 9. As a result, the main component of the atmosphere in the sample gas 100 is removed, and the concentration of the target gas in the sample gas 100 increases. The target gas concentrated in the chamber 3 is detected by the gas sensor 2**.

When the removing function of filter 7 is recovered, the operation of the gas sensor 2 is ended and the vacuum pump 5 and the temperature regulator 11 are operated. According to the temperature rise of the suction pipe 6, the background gas adsorbed on the porous metal complexes **8*b* and 9*b* is desorbed and exhausted through the chamber 3. In this way, the removing function of filter 7 can be restored without removing the suction pipe 6**.

Summary of Embodiment

According to the gas measuring device 1, target gas contained in the sample gas 100 in the atmosphere is not adsorbed by the filter 7, nitrogen gas, oxygen gas, or rare gases are removed from the sample gas 100, and the target gas is detected in the sample gas 100 by the gas sensor 2. Nitrogen gas, oxygen gas or rare gases is contained in a large amount in the atmosphere and becomes a factor of lowering the detection sensitivity of the gas sensor 2. Since the main component gas in the atmosphere is removed by the filter 7, the gas that lower the detection sensitivity are removed and the target gas is relatively concentrated. Therefore, the gas measuring device 1 can improve the detection accuracy of the target gas in the atmosphere. In addition, according to the gas measuring device 1, since the target gas is relatively concentrated, it is not necessary to prepare a dedicated concentrator or the like for each gas type of the target gas, and it is possible to easily increase detection accuracy of the target gas. That is, the gas measuring device 1 can provide a concentration function that can be used universally regardless of the type of gas sensor.

Since the filter 7 including the porous metal complexes **8*b* and 9*b* are adopted as the gas measuring device 1**, it is less likely to be affected by electrical activity and can remove low-molecular-weight gases as compared with a general adsorption member, allowing for the appropriate removal of nitrogen gas, oxygen gas, and rare gases.

In the gas measuring device 1, since the filter 7 includes the bags **8*a* and 9*a* which contain the porous metal complexes 8*b* and 9*b* in powder form and have air permeability, the amounts and containing forms of the porous metal complexes 8*b* and 9*b* can be adjusted according to the flow rate of the sample gas 100 or the internal shape of the suction pipe 6, and the risk of diffusion of the porous metal complexes 8***b* and 9*b* in powder form to the measurement system or the atmosphere can be reduced.

In the gas measuring device 1, since the filter 7 has a dual filter structure of the first filter 8 and the second filter 9, for example, when maintenance for restoring the function of removing oxygen gas is required, the operator does not need to replace the entire the filter 7 but can replace only the first filter 8 requiring maintenance. Therefore, the gas measuring device 1 can improve the maintainability.

Modification

While various exemplary embodiments have been described above, various omissions, substitutions and changes may be made without being limited to the exemplary embodiments described above.

A plurality of gas sensors including the gas sensor 2 and a gas sensor different from the gas sensor 2 may be disposed in the chamber 3. The porous metal complexes 8*b* and 9*b* may be provided as an adsorption member instead of powder. In this case, the gas measuring device 1 may not include the bags 8*a* and 9*a*. The porous metal complexes 8*b* and 9*b* may be arranged in any manner as long as they are arranged on the upstream side of the gas sensor 2. The filter 7 may be composed of either a single filter or three or more filters.

Figure 2:
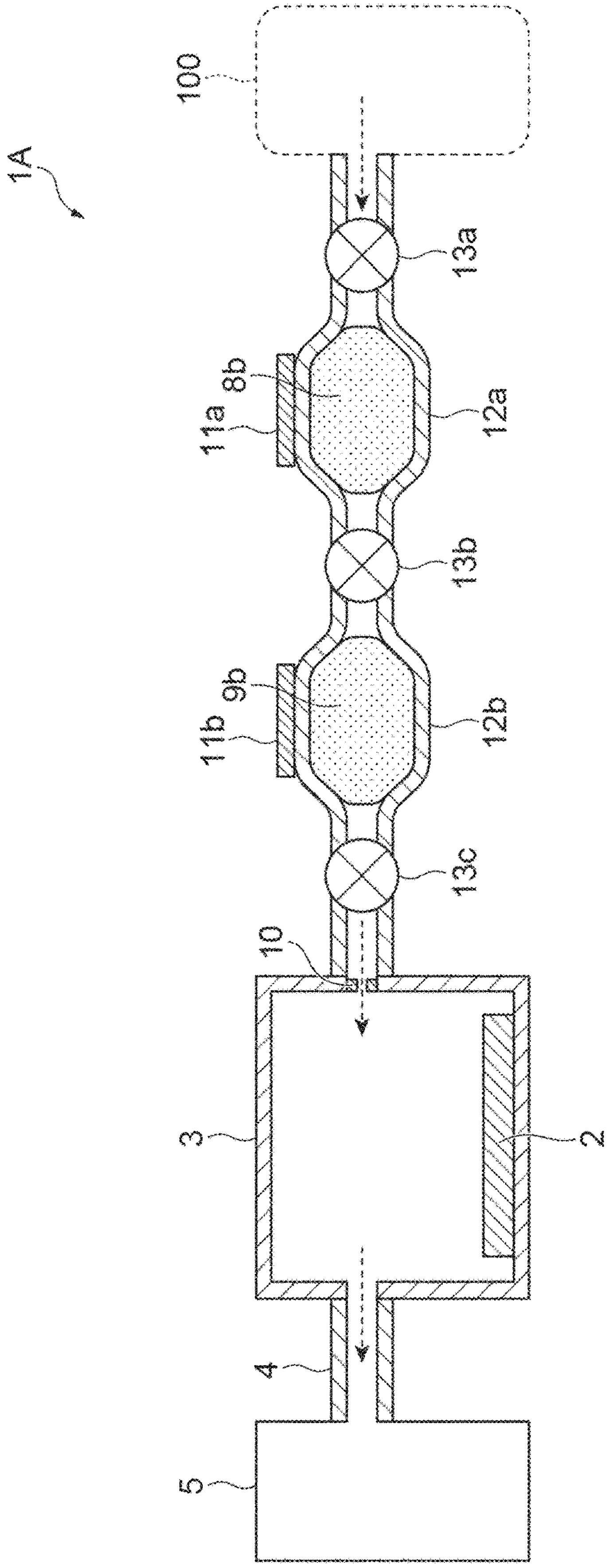
FIG. 2 is a schematic view showing a modified example of the gas measuring device according to the embodiment.

FIG. 2 is a schematic view showing a modified example of the gas measuring device. A gas measuring device 1A shown in FIG. 2 is different from the gas measuring device 1 shown in FIG. 1 in that the porous metal complexes 8*b* and 9*b* constituting the filter 7 are stored in containers, respectively, and the rest is the same. In the following description, differences will be mainly described and redundant description will be omitted.

As shown in FIG. 2, the suction pipe 6 located upstream of the gas sensor 2 is provided with a first container 12*a* and a second container 12*b*. The first container 12*a* and the second container 12*b* are hollow. The first container 12*a* contains the porous metal complex 8*b*. The second container 12*b* contains the porous metal complex 9*b*.

The first container 12*a* and the second container 12*b* have an injection port and an exhaust port. The injection port of the first container 12*a* is configured to allow the introduction of the sample gas 100 from the atmosphere. The exhaust port of the first container 12*a* is connected to the injection port of the second container 12*b*. The exhaust port of the second container 12*b* is connected to the chamber 3. In this way, the first container 12*a* and the second container 12*b* are connected in series and in communication.

A first valve 13*a* is provided at the injection port of the first container 12*a*. The first valve 13*a* is controlled to regulate the flow rate of the sample gas 100 into the first container 12*a*. A second valve 13*b* is provided in the exhaust port of the first container 12*a*. By controlling the second valve 13*b*, the flow rate of the sample gas 100 exhausted from the first container 12*a*, that is, the flow rate of the sample gas 100 flowing into the second container 12*b* is adjusted. A third valve 13*c* is provided in the exhaust port of the second container 12*b*. By controlling the third valve 13*c*, the flow rate of the sample gas 100 exhausted from the second container 12*b*, that is, the flow rate of the sample gas 100 flowing into the chamber 3 is adjusted. Some or all of the first valve 13*a*, the second valve 13*b*, and the third valve 13*c* may be mass flow controllers.

The first container 12*a* and the second container 12*b* are provided with temperature regulators 11*a* and 11*b* to regulate temperature. Each constitution of the temperature regulators 11*a* and 11*b* is the same as that of the temperature regulator 11, and the background gas adsorbed in the porous metal complexes 8*b* and 9*b* can be removed.

In the gas measuring device 1A configured as described above, the sample gas 100 flows into the first container 12*a*, and oxygen gas is removed from the sample gas 100 by the porous metal complex 8*b* and sent to the second container 12*b*. Nitrogen gas or rare gases are then removed from the sample gas 100 by the porous metal complex 9*b* in the second container 12*b* and sent to the chamber 3. In addition, since the first container 12*a* and the second container 12*b* have a structure in which an injection port and an exhaust port thereof can be opened and closed, it is possible to reduce a risk that the porous metal complexes 8*b* and 9*b* in powder form are diffused into a measurement system or the atmosphere. Thus, the first container 12*a* and the porous metal complex 8*b* constitute the first filter 8, the second container 12*b* and the porous metal complex 9*b* constitute the second filter 9, and the first container 12*a*, the porous metal complex 8*b*, the second container 12*b* and the porous metal complex 9*b* constitute the filter 7 in the gas measuring device 1. Therefore, the gas measuring device 1A has the same effect as the gas measuring device 1.

REFERENCE SIGNS LIST

1, 1A . . . gas measuring device, 2 . . . gas sensor, 7 . . . filter, 8 . . . first filter, 9 . . . second filter, 8*a*, 9*a* . . . bag, 8*b*, 9*b* . . . porous metal complex, 12*a* . . . first container, 12*b* . . . second container, 100 . . . sample gas.

The invention claimed is:

1. A gas measuring device comprising:

a filter comprising a porous metal complex in which a metal ion and an organic ligand are bonded, and configured to remove background gas from sample gas in an atmosphere; and a gas sensor configured to detect target gas from the sample gas passed through the filter, wherein the background gas is at least one kind of gas selected from nitrogen gas, oxygen gas, and rare gases, and wherein the filter includes:

a first filter formed of the porous metal complex that mainly removes oxygen gas; and a second filter disposed downstream of the first filter and formed of the porous metal complex that mainly removes nitrogen gas and rare gases.

2. The gas measuring device according to claim 1, wherein each of the first filter and the second filter comprises a breathable bag configured to contain the porous metal complex in powder form.

3. The gas measuring device according to claim 1, wherein each of the first filter and the second filter has a container configured to accommodate the porous metal complex in powder form, and the container includes an injection port for injecting the sample gas and an exhaust port for exhausting the sample gas.

4. The gas measuring device according to claim 1, wherein the first filter is formed of the porous metal complex in which metal ion and tetracyanoquinodimethane are bonded, and the second filter is formed of the porous metal complex in which metal ion and terephthalic acid are bonded, or metal ion and methylene are bonded.

* * * * *